United States Patent
Ballance et al.

(10) Patent No.: US 6,439,789 B1
(45) Date of Patent: Aug. 27, 2002

(54) POLYMERIZABLE 1, 1-DISUBSTITUTED ETHYLENE MONOMER FORMULATION APPLICATORS, APPLICATOR TIPS, APPLICATOR KITS AND METHODS

(75) Inventors: Jerry Ballance, Willow Spring; Daniel L. Hedgpeth, Raleigh; Jeffrey G. Clark, Raleigh; William Cotter, Raleigh, all of NC (US)

(73) Assignee: Closure Medical Corporation, Raleigh, NC (US)

(*) Notice: Subject to any disclaimer, the term of this patent is extended or adjusted under 35 U.S.C. 154(b) by 0 days.

(21) Appl. No.: 09/671,340

(22) Filed: Sep. 27, 2000

(51) Int. Cl.[7] .................................................. B43K 5/14
(52) U.S. Cl. ....................................................... 401/134
(58) Field of Search ................................... 401/132–135

(56) References Cited

U.S. PATENT DOCUMENTS

| | | | |
|---|---|---|---|
| 3,818,911 A | 6/1974 | Fournier | 128/269 |
| 4,925,327 A | 5/1990 | Wirt | 401/205 |
| 4,957,385 A | * 9/1990 | Weinstein | 401/132 |
| 4,961,661 A | 10/1990 | Sutton et al. | 401/6 |
| 5,042,690 A | 8/1991 | O'Meara | 222/83 |
| 5,445,462 A | 8/1995 | Johnson et al. | |
| 5,538,353 A | 7/1996 | Dehavilland | |
| D386,849 S | 11/1997 | Dehavilland | |
| 5,690,958 A | 11/1997 | McGrath | |
| 5,772,346 A | 6/1998 | Edwards | |
| D396,911 S | 8/1998 | Dehavilland | |
| 5,908,256 A | 6/1999 | Bernstein | 401/205 |
| 6,090,397 A | 7/2000 | Lee et al. | |
| 6,155,265 A | 12/2000 | Hammerslag | 128/898 |

FOREIGN PATENT DOCUMENTS

| | | | | |
|---|---|---|---|---|
| WO | 96/40797 | * 12/1996 | | C08F/4/02 |
| WO | WO 99/22801 | 5/1999 | | |
| WO | WO 00/12411 | 3/2000 | | |

OTHER PUBLICATIONS

U.S. application No. 09/658,519, D'Alessio et al., filed Sep. 8, 2000.

* cited by examiner

Primary Examiner—Gregory L. Huson
Assistant Examiner—Peter deVore
(74) Attorney, Agent, or Firm—Oliff & Berridge, PLC

(57) ABSTRACT

A polymerizable 1,1-disubstituted ethylene formulation applicator includes polymerizable 1,1-disubstituted ethylene monomer. According to one embodiment, the monomer is surrounded by a container that may be engaged with an applicator tip The applicator tip has an internal cavity defined in an applicator tip body. A female fitting at an open end of the applicator tip body is in fluid communication with the cavity. A porous material member is connected to the applicator tip body to be in fluid communication with the internal cavity. The applicator tip may include a valve member disposed between the internal cavity and the porous material member. Also, the applicator tip may include a piercing or breaking member disposed substantially within the internal cavity. The container of monomer includes a male fitting that may be engaged with the female fitting of the applicator tip to form the applicator. The container also may include a polymerizable 1,1-disubstituted ethylene impervious barrier that may be pierced or broken by the piercing or breaking member when the male fitting is engaged with the female fitting. Depending on the particular application and the particular formulation, bioactive agents, viscosity modifiers, initiators, inhibitors and/or stabilizers may be added to the applicator, preferably in or on the porous material member. The container and one or more applicator tips form an applicator kit. Methods of applying a polymerizable 1,1-disubstituted ethylene formulation employ the various embodiments of the applicator tip, the applicator and the applicator kit, especially for the treatment of lacerated, burned, ulcerous, and laser-ablated tissues.

70 Claims, 5 Drawing Sheets

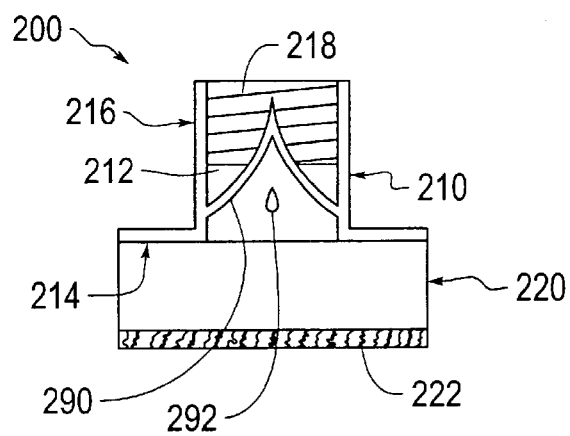 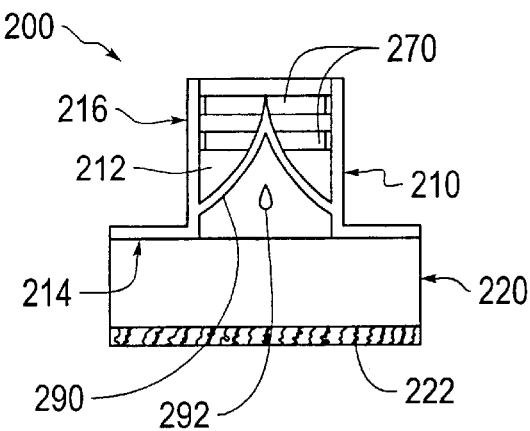
Fig. 5         Fig. 6
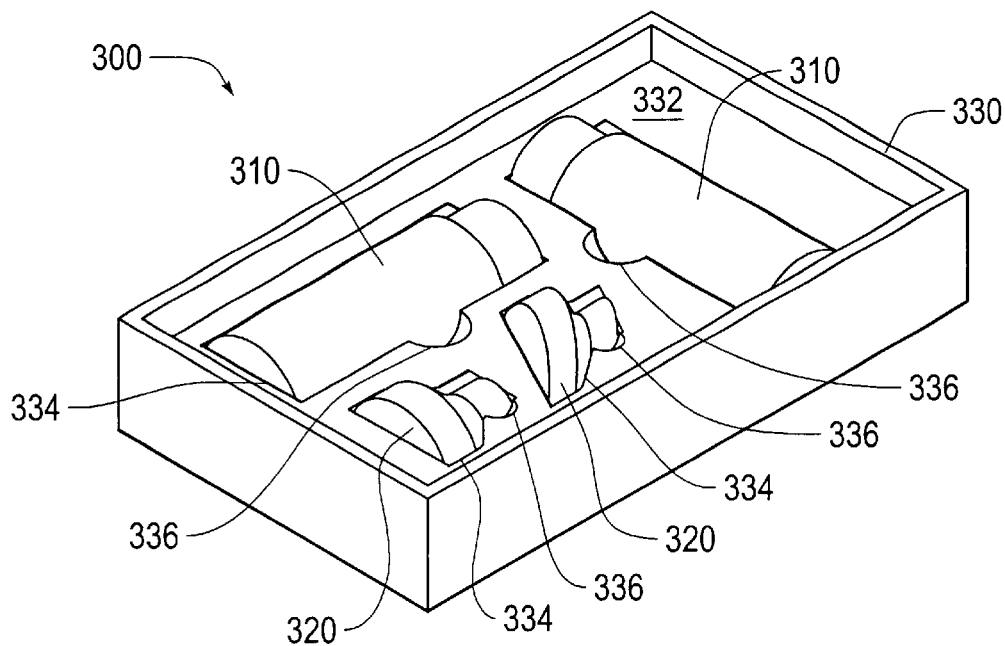
Fig. 7

POLYMERIZABLE 1,1-DISUBSTITUTED ETHYLENE MONOMER FORMULATION APPLICATORS, APPLICATOR TIPS, APPLICATOR KITS AND METHODS

BACKGROUND OF THE INVENTION

1. Field of Invention

The present invention relates to polymerizable 1,1-disubstituted ethylene formulation applicators, applicator tips, applicator kits and methods.

2. Description of Related Art

A type of liquid applicator having a body with a cavity in which a frangible ampoule is disposed is known. For example, U.S. Pat. No. 5,538,353 to DeHavilland and U.S. Pat. No. 5,445,462 to Johnson et al. include the liquid to be dispensed within an ampoule and include means for breaking the ampoule to release the liquid.

Johnson et al. discloses an applicator with an elongated body that connects a cap at one end to a tip at the other end. A frangible ampoule containing fluid is supported within the one end adjacent the cap, remote from the tip. By pressing the cap in a longitudinal direction of the elongated body, the ampoule is broken to allow the fluid to flow through the elongated body to the tip. Embodiments for dispensing both relatively small amounts and relatively larger amounts of the fluid are disclosed. This reference discloses that such applicators are known for dispensing liquids such as medicaments or antiseptics.

A device similar to the applicator of Johnson et al. is advertised by MedLogic Global Corporation to dispense adhesive compositions, including cyanoacrylate formulations. In particular, MedLogic advertises use of such an applicator for applying a liquid surgical drape.

DeHavilland discloses a hand-held applicator for liquids such as medicaments or cleaning agents with a body connected to a porous element. A frangible ampoule containing fluid is supported within the body. The applicator body includes a pair of elongated gripping members that have a wing-like configuration. The frangible ampoule is located between the gripping members such that the ampoule is broken by squeezing the gripping members towards each other, allowing the fluid to flow into the porous element. The gripping members are particularly designed to provide a mechanical advantage for breaking the ampoule and to reduce the risk of injury from shards of the broken ampoule. This reference discloses that such applicators are known for dispensing liquids such as medicaments, cleansing agents, cosmetics, polishes or the like.

U.S. Pat. No. 5,690,958 to McGrath and U.S. Pat. No. 5,772,346 to Edwards disclose improvements made to the applicator of DeHavilland. In particular, McGrath provides a unit dose chlorhexadine gluconate (CHG) applicator. The unit dose of chlorhexadine gluconate antiseptic is contained in a hermetically sealed glass ampoule. Edwards provides breaking and retaining tappets between the gripping members and each side of the ampoule. These tappets are arranged to localize the fracturing force applied by the gripping members and to prevent the ampoule from moving towards the porous element.

A cyanoacrylate composition applicator kit is disclosed in U.S. Pat. No. 5,928,611 to Lee et al. The kit includes a first container of a cyanoacrylate composition and a second container of a compatible antimicrobial agent. The kit is used to store the cyanoacrylate composition and the antimicrobial agent separately until they are mixed for use.

Applicators for dispensing a polymerizable and/or cross-linkable material, such as a 1,1-disubstituted ethylene formulation, are disclosed in U.S. Pat. No. 5,928,611 to Leung and copending U.S. patent application Ser. No. 09/430,177, filed Oct. 29, 1999. In general, many different 1,1-disubstituted ethylene formulations are known for various applications, for example, cyanoacrylate formulations used as fast-acting surgical adhesives, sealants, bioactive agent release matrices and implants utilized in medical, surgical and other in vivo applications. Such formulations include those disclosed by Leung and the references cited therein.

SUMMARY OF THE INVENTION

The present invention is based on the discovery that an applicator for polymerizable 1,1-disubstituted ethylene formulations is needed that overcomes disadvantages and limitations of known applicators for such materials. This invention provides a 1,1-disubstituted ethylene formulation applicator that is particularly useful.

Embodiments of the present invention provide a polymerizable 1,1-disubstituted ethylene formulation applicator which provides a user with the flexibility to select between various tip configurations for a particular use. This flexibility allows a user to select an appropriate tip configuration so that, for example, a broad swath of a polymerizable 1,1-disubstituted ethylene monomer formulation may be quickly applied. Also, for example, a tip configuration may be selected that provides a substantially uniform layer of cyanoacrylate adhesive formulation and/or a predetermined area of coverage.

Embodiments of the present invention also provide an applicator which simplifies dispensing of the formulation. The simplified dispensing helps to reduce potential spillage of the formulation to avoid waste and undesired application of the formulation.

Embodiments of the present invention provide an applicator with a controlled flow of polymerizable 1,1-disubstituted ethylene monomer formulation. Such embodiments help to reduce unwanted application of the formulation and/or over-application of the formulation.

According to embodiments of this invention, a two-piece applicator comprising an applicator tip and a container of polymerizable 1,1-disubstituted ethylene monomer formulation is provided. According to this invention, embodiments provide a kit comprising a plurality of applicator tips and at least one container of polymerizable 1,1-disubstituted ethylene monomer formulation.

Embodiments of this invention include a coupler that connects an applicator tip to a container of polymerizable 1,1-disubstituted ethylene monomer formulation. Further, embodiments of this invention include a casing that is arranged to receive a cartridge of polymerizable 1,1-disubstituted ethylene monomer formulation and to cooperate with an applicator tip to form a polymerizable 1,1-disubstituted ethylene monomer formulation applicator.

Embodiments of this invention provide an applicator tip that may be used directly with a polymerizable 1,1-disubstituted ethylene monomer formulation container or as an attachment to an existing applicator tip. According to this invention, embodiments of the applicator tip may be pivotable, shaped and/or made of a material for advantageously applying the monomer.

These and other features of the invention are particularly advantageous for the application of polymerizable 1,1-disubstituted ethylene monomer formulations in certain medical procedures, such as laser ablation, and the treatment of burns and ulcers.

BRIEF DESCRIPTION OF THE DRAWINGS

Exemplary embodiments of the present invention are described in detail below, with reference to the attached drawing figures, in which:

FIG. 5 is a cross-sectional view of another exemplary embodiment of a 1,1-disubstituted ethylene formulation applicator tip in accordance with the present invention;

FIG. 6 is a cross-sectional view of another exemplary embodiment of a 1,1-disubstituted ethylene formulation applicator tip in accordance with the present invention;

FIG. 7 is a perspective view of an exemplary embodiment of a 1,1-disubstituted ethylene formulation applicator kit in accordance with the present invention;

DETAILED DESCRIPTION OF PREFERRED EMBODIMENTS

Figure 1:
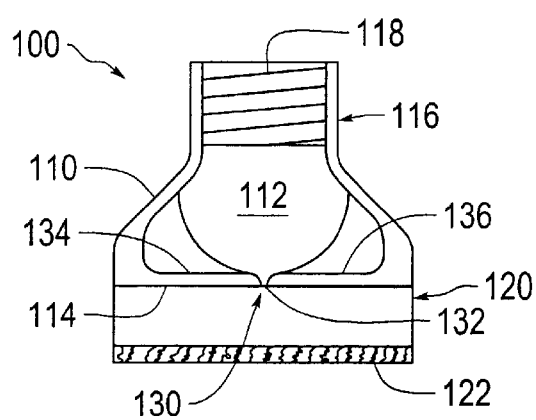
FIG. 1 is a cross-sectional view of an exemplary embodiment of a 1,1-disubstituted ethylene formulation applicator tip in accordance with the present invention.

The present invention provides polymerizable 1,1-disubstituted ethylene monomer formulation applicators which overcome disadvantages and limitations of known applicators. Known applicators noted above do not provide sufficient flexibility in selecting an appropriate tip configuration for a particular use.

Further, known multi-piece applicators suffer from drawbacks. For example, the mating configuration disclosed by Lee et al. for combining two containers of different compositions may result in spillage, causing waste and/or unwanted application of one of the compositions.

Further drawbacks of known applicators is that the flow of the formulation is not controlled. These known applicators rely almost exclusively on gravity for the formulation to flow to the applicator pad on the tip. Thus, the rate of flow is dependent on the amount of composition remaining in the container/applicator that creates head pressure. Also, the flow of the formulation may only be stopped by turning the applicator upside down. This inhibits a user's ability to properly position the applicator prior to application of the formulation.

Polymerizable 1,1-disubstituted ethylene monomer formulation applicators, applicator tips and applicator kits of the present invention overcome such disadvantages and limitations.

According to embodiments of this invention, a polymerizable 1,1-disubstituted ethylene monomer formulation applicator comprises an applicator tip and a container of an amount of polymerizable 1,1-disubstituted ethylene monomer. The container and applicator tip have engageable fitting portions so that the applicator tip may be connected to the container to form the applicator. Preferably, the fitting portion of the applicator tip is a female fitting portion, and the fitting portion of the container is a male fitting portion.

This arrangement helps to avoid spillage of the polymerizable 1,1-disubstituted ethylene monomer formulation as the applicator tip is connected to the container. The female fitting portion will provide a catch basin for the formulation. Thus, if the container is opened prior to connecting the applicator tip, the orientation of the container need not be maintained to make the connection. If the container is sealed by a barrier that is broken by connecting the applicator tip, the female fitting will also act as a catch basin for the formulation should the barrier be broken before the applicator tip and the container are fully connected.

According to embodiments of this invention, a polymerizable 1,1-disubstituted ethylene monomer formulation applicator tip comprises an applicator tip with an internal cavity and a porous material member in fluid communication with the internal cavity. Embodiments of the applicator tip further comprise a valve member disposed between the internal cavity and the porous material member.

The valve member of the applicator tip provides flow control. Not only may the valve member be responsive to manual pressure or other manual action to provide a desired flow of formulation for application, the valve member may allow the flow of the formulation to be completely stopped. Thus, unwanted application or over-application of the formulation may be reduced or even completely avoided.

In embodiments, the applicator tip includes a piercing or breaking member disposed at least partially within the female fitting of the applicator tip body. The piercing/breaking member is used to pierce/break a barrier, partition, membrane or the like that seals an opening of the container. Thus, when the applicator tip is attached to a container of a polymerizable 1,1-disubstituted ethylene monomer formulation, the formulation is released into the cavity of the applicator tip.

Embodiments of the invention provide a 1,1-disubstituted ethylene monomer formulation applicator kit. According to the invention, the kit comprises an applicator tip and a container of a 1,1-disubstituted ethylene monomer formulation which may be connected to form a 1,1-disubstituted ethylene monomer formulation applicator. Embodiments of the kit include at least two applicator tips. Further, embodiments of the kit include applicator tips with different configurations. Embodiments of the kit include at least two containers, especially containers of different sizes and/or formulations.

When multiple applicator tips are provided in the kit, a user may make multiple separate applications using the same container of formulation. This helps to avoid wasting formulation because of an applicator tip that becomes "clogged" by monomer that polymerizes in the applicator tip during use, or that becomes contaminated prior to or during use, prior to use of the entire amount of formulation.

When the multiple applicator tips in the kit have different configurations, a user may select and/or switch between tip configurations while using the same container of formulation. This also helps to avoid wasting formulation since a separate applicator with its own container is not needed for each different application need encountered. Further, a user need only stock a single kit that may be used for multiple application needs, rather than a certain type of applicator for each application need.

When multiple containers of different formulations are included in the kit, a user may select the appropriate formulation for a particular application. This allows the kit to be used for a greater number of different application needs. When multiple containers of different sizes are included in the kit, a user may select the appropriate size for a particular application. This helps to avoid wasting formulation by selection of the right amount rather than a "one-size-fits-all" amount of formulation.

Embodiments of the invention provide a 1,1-disubstituted ethylene monomer formulation applicator that may readily be manipulated from an inactivated state to an activated state for application of the monomer. According such embodiments, the applicator comprises an applicator tip and a container of a 1,1-disubstituted ethylene monomer formulation connected by a coupler. The coupler may include one or more retaining members that engage a portion of the container so that the container is movable between an inactivated position and an activated position.

Additional embodiments of this invention provide a 1,1-disubstituted ethylene monomer formulation applicator that does not require a direct mechanical connection between a container of a 1,1-disubstituted ethylene monomer formulation and an applicator tip. According to such embodiments, the applicator comprises a casing into which a cartridge of a 1,1-disubstituted ethylene monomer formulation may be placed. The casing may include a removable cap for insertion of the cartridge. The cap may cooperate with an applicator tip or may be replaced by an applicator tip to form the 1,1-disubstituted ethylene monomer formulation applicator.

Embodiments of this invention provide an applicator tip that is particularly suitable for applying a 1,1-disubstituted ethylene monomer. According to the invention, the applicator tip may cooperate directly with a container of formulation or may used as an attachment to an existing applicator tip. Embodiments of the applicator tip/attachment include a pivotable head portion having an application surface that is advantageous for applying the monomer. Preferably, the material and shape of the head portion and/or the application surface are particularly adapted for applying the monomer.

Applicators according to this invention are particularly suitable for laser ablation procedures. Such procedures are typically cosmetic and are used to reduce or eliminate wrinkles, scars, and other defects in the skin, particularly the face. A laser is used to burn off a few layers of cells of the skin, including some of the dermis layer. The treated skin is then washed to remove the burned skin cells and finally a bandage is applied to protect the treated skin and absorb exudate therefrom.

Exudate is produced by the treated skin within approximately 1–2 hours after the procedure. If the exudate is allowed to scab, then the potential for scaring of the treated skin is increased, defeating the purpose of the procedure. By using a polymerizable 1,1-disubstituted ethylene monomer formulation according to this invention, exudate formation may be prevented and thus potential scarring may be avoided.

According to the present invention, after the treated skin has been washed, a thin film of polymerizable 1,1-disubstituted ethylene monomer is applied to seal the treated skin. Upon polymerization, the applied formulation forms a bandage that seals the treated skin. Since the formulation is applied directly to the treated skin, the occlusive bandage formed is shaped perfectly to the contours of the treated skin. Thus, polymerizable 1,1-disubstituted ethylene formulations and applicators according to this invention provide a perfect "fit" for ideally sealing the treated skin.

Further, as the treated skin heals, the growth of new skin will loosen the occlusive bandage. Thus, once the treated skin has healed, removal of the occlusive bandage is simple and relatively painless.

Polymerizable 1,1-disubstituted ethylene monomer formulations may be used for various applications, for example, as fast-acting surgical adhesives for closure and/or protective coverage of wounds (e.g., cuts, abrasions, stomatitus, sores, decubitus, diabetic and other ulcers, burns and the like), sealants, bioactive agent release matrixes and implants utilized in medical, surgical and other in vivo applications. Preferred monomers include alpha-alkyl cyanoacrylate monomers, such as ethyl, n-butyl and/or 2-octyl cyanoacrylate monomers. Preferred formulations also include additives such as stabilizers, plasticizers, thickeners and colorants. Such formulations include those disclosed by U.S. Pat. Nos. 5,328,687, 5,514,371, 5,514,372, 5,575,997, 5,582,834, 5,624,669 and 5,928,611, all to Leung et al., and U.S. patent application Ser. No. 09/471,392 filed Dec. 23, 1999, the disclosures of which are incorporated herein by reference in their entirety. As used herein, the term "monomer" includes polymerizable prepolymers and oligomers.

In certain applications or for certain formulations of 1,1-disubstituted ethylene, the addition of one or more bioactive agents, viscosity modifiers, initiators, inhibitors or stabilizers, polymerization rate modifiers and/or other additives is highly desirable. As disclosed in U.S. Pat. No. 5,928,611 to Leung, for example, viscosity modifiers such as poly(ethyl 2-cyanoacrylate) and poly(lactic acid) have been used in combination with alkyl alpha-cyanoacrylate monomers. Also, acids may be used to inhibit or slow and bases may be used to accelerate polymerization of alpha-cyanoacrylate monomers. These and other useful additives are disclosed in U.S. patent application Ser. No. 09/430,177 filed Oct. 29, 1999, and U.S. patent application Ser. No. 09/099,457 filed Jun. 18, 1990, the entire disclosure of each of which is also incorporated herein by reference. One or more additives, such as polymerization/cross-linking initiators or rate modifiers (hereafter, collectively referred to as polymerization affecting agents), bioactive agents, colorants or the like, may be included in the applicators according to this invention.

An exemplary embodiment of a polymerizable 1,1-disubstituted ethylene monomer formulation applicator tip 100 is shown in cross section in FIG. 1. The polymerizable 1,1-disubstituted ethylene monomer formulation applicator tip 100 comprises an applicator tip body 110 having an internal cavity 112. The applicator tip body 110 is provided with a substantially planar base 114 that closes an end of the internal cavity 112. While the exemplary embodiment shown in FIG. 1 includes the base 114, it should be understood that the base 114 is optional.

In embodiments, a porous material member 120 is connected to the applicator tip body 110 so that the porous material member 120 may be in fluid communication with the internal cavity 112. As shown in FIG. 1, when the base 114 is included, the porous material member 120 may be connected to the base 114 and may be sized accordingly. Further, the porous material member 120 may be a sponge as illustrated in FIG. 1, or may be any other suitable material such as a fabric, for example, a nylon fabric, or a membrane.

The porous material member 120 may or may not be included. Further, when included, the porous material member 120 may be disposed anywhere as long as it is in fluid communication with the internal cavity 112. For example, the porous material member 120 may be disposed in the internal cavity 112.

One or more additives, such as polymerization affecting agents, bioactive agents, colorants or the like, may be included in the porous material member 120. In particular, the entire porous material member 120, or a surface or layer thereof, may be impregnated with the additive(s). For example, an application surface 122 of the porous material member 120 remote from the internal cavity 112 may be coated with the additive(s). Alternatively, if the porous material member 120 is omitted, or in addition, if the porous material member 120 is in the internal cavity 112, the application surface 122 coated with such additives may be part of the applicator tip body 110. In any case, the desired amount of the additive may be determined based on the amount of the polymerizable 1,1-disubstituted ethylene monomer formulation, the particular formulation thereof, or the particular application.

In the exemplary embodiment shown, the porous material member 120 is adjacent to the internal cavity 112, but separated from the internal cavity 112 by a valve member 130. The valve member 130 is shown in FIG. 1 as a variable slit 132 formed in the base 114 of the applicator tip body 110. However, it should be understood that any other known or hereafter developed valve device may be used. For example, a mechanical valve, such as a spring valve, may be used. Embodiments of the valve member 130 are pressure-controlled, as described below.

In the exemplary embodiment, the valve member 130 is formed by a first flexible portion 134 and a second flexible portion 136. The flexible portions 134 and 136 are arranged to bend inwardly towards the internal cavity 112, or outwardly towards the porous material member 120, to widen the slit 132 placing the internal cavity 112 in fluid communication with the porous material member 120. The operation of the valve member 130 is described further below.

A female fitting portion 116 of the applicator tip body 110 defines an end that opens into the internal cavity 112. As shown, the female fitting portion 116 may be opposite the valve member 130 and the porous material member 120. The female fitting portion 116 shown in the embodiment of FIG. 1 includes female screw threads 118. In other words, screw threads 118 are formed on an inner surface of the female fitting portion 116. As described below, the female fitting portion 116 and screw threads 118 are designed to mate with a container to form an applicator according to this invention.

Figure 2:
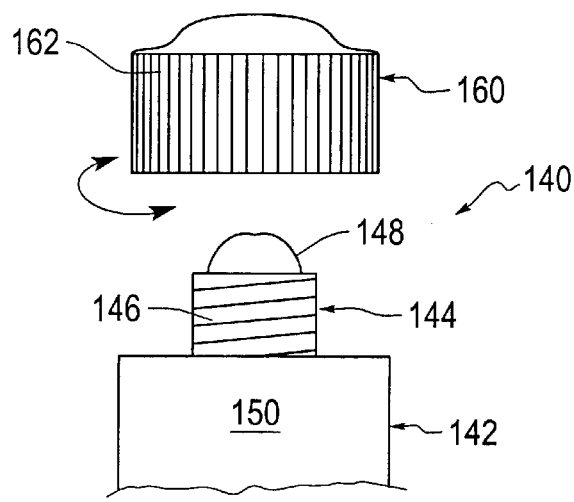
FIG. 2 is a partial elevational view of a 1,1-disubstituted ethylene formulation container that forms an exemplary embodiment of a 1,1-disubstituted ethylene formulation applicator in accordance with the present invention when connected to the applicator tip of FIG. 1.

An exemplary embodiment of a polymerizable 1,1-disubstituted ethylene monomer formulation container 140 is shown in FIG. 2. A body 142 of the container 140 is shown cutaway since the container body 142 may be of any desired shape or configuration. For example, the container body 142 may include features that improve gripping or facilitate controlled squeezing. The container body 142 houses an amount of a polymerizable 1,1-disubstituted ethylene monomer 150, preferably in a composition as discussed above. Thus, only the internal size of the container body 142 is constrained by the desired amount of the polymerizable 1,1-disubstituted ethylene monomer formulation 150.

The container 140 should be made of a material providing storage stability for the particular 1,1-disubstituted ethylene monomer formulation 150. For certain formulations, glass is a suitable material. Metal, such as aluminum or tin, may also be advantageous for the container 140. Also, as disclosed in U.S. patent application Ser. No. 09/430,289 filed Oct. 29, 1999, which is incorporated herein by reference in its entirety, polymeric and modified polymeric materials, such as fluorinated low density polyethylene, high density polyethylene or PET, may be used. Further, the container 140 may be made of a combination of materials. For example, the container 140 may be made of metal and internally laminated with a plastic material, such as fluorinated low density polyethylene, fluorinated high density polyethylene, PET or PTFE. Similarly, the container 140 may be made of various layers of different materials.

Alternatively or in addition, a stabilizer, such as those disclosed in the incorporated references, may be added to the 1,1-disubstituted ethylene formulation 150 or to the material of the container 140 to prevent polymerization/cross-linking of the monomer. Any desired amount of stabilizer may be added to the material of the container 140 or coated on the inside walls of the container body 142, as long as the coated/impregnated stabilizer is not released into the 1,1-disubstituted ethylene formulation 150.

In the exemplary embodiment, the container body 142 is provided with a male fitting portion 144. Further, the container body 142 may include a dispensing tip 148 that may include an opening (not shown) or may be readily piercable to allow the monomer 150 to flow from the container 140. The male fitting portion 144 includes male screw threads 146 corresponding to the female screw threads 118 of the female fitting portion 116 of the applicator tip 100 shown in FIG. 1.

A female cap member 160 may be used to close the container 140 prior to use, between uses, and/or after use. In particular, prior to use, the female cap member 160 may hermetically seal the container 140. The female cap member 160 includes internal threads (not shown) that mate with the male screw threads 146. Further, the female cap member 160 may include vertical ribs or grooves 162 that facilitate manual rotation of the cap member 160 relative to the container 140.

The exemplary embodiments of the applicator tip 100 and the container 140 shown in FIGS. 1 and 2, respectively, may be connected to form a polymerizable 1,1-disubstituted ethylene monomer formulation applicator according to the present invention. First, the female cap member 160 is unscrewed and removed from the male fitting portion 144 of the container 140. If necessary, the dispensing tip 148 is then pierced. (This may be accomplished as described below with respect to the embodiments shown in FIGS. 5 and 6.) Then, the male fitting portion 144 is aligned with the female fitting portion 116 of the applicator tip 100 so that the male screw threads 146 engage the female screw threads 118. By turning the applicator tip 100 relative to the container 140, vice versa, or both simultaneously, the male fitting portion 144 is releaseably secured within the female fitting portion 116.

During assembly, or at least once assembled, the formulation 150 may flow due to gravity into the internal cavity 112 of the applicator tip 100. Then, the container 140 may be squeezed to apply pressure that causes the formulation 150 to flow and press against the first and second flexible portions 134, 136. Once the first and second flexible portions 134, 136 are forced outward to widen the variable slit 132 of the valve member 130, the formulation 150 flows into the porous material member 120. Once the pressure is released, the variable slit 132 of the valve member 130 closes to prevent undesired flow of the formulation 150 into the porous material member 120.

It should be recognized that, in addition to stopping the flow of the formulation, the valve member 130 provides control of the flow of the formulation 150 by opening in response to pressure. Thus, a user may control the flow rate by applying varying amounts of pressure (squeezing the container body) so that the variable slit 132 opens a corresponding amount as desired.

Alternatively, the first and second flexible portions 134, 136 may be arranged such that compression of the porous material member 120 forces the first and second flexible portions 134, 136 inward to widen the variable slit 132 of the valve member 130. Again, once the pressure is released, the variable slit 132 of the valve member 130 closes to prevent undesired flow of the formulation 150 into the porous material member 120. In such a case, a user may control the flow rate by applying varying amounts of pressure (compressing the porous material member) so that the variable slit 132 opens a corresponding amount as desired.

Figure 3:
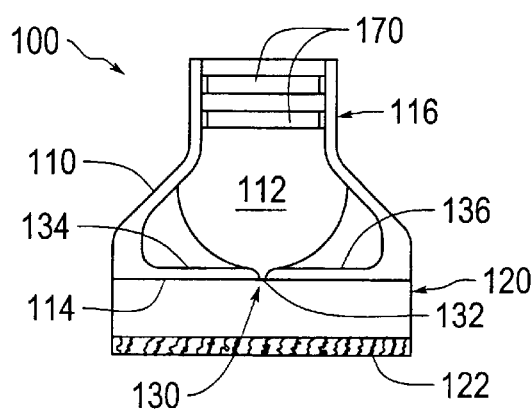
FIG. 3 is a cross-sectional view of another exemplary embodiment of a 1,1-disubstituted ethylene formulation applicator tip in accordance with the present invention.

Another exemplary embodiment of the polymerizable 1,1-disubstituted ethylene monomer formulation applicator tip 100 is shown in cross section in FIG. 3. The applicator tip 100 shown in FIG. 3 differs from applicator tip shown in FIG. 1 in that the female fitting portion 116 includes one or more internal elements 170. As illustrated, the internal elements 170 may be two annular protrusions. It should be understood, however, that other configurations of the internal elements 170 are contemplated, such as spaced tabs, annular grooves and/or non-continuous recesses, and a luer lock arrangement, and that only one internal element may be used. As described below, the female fitting portion 116 and internal elements 170 are designed to mate with a container to form an applicator according to this invention.

Figure 4:
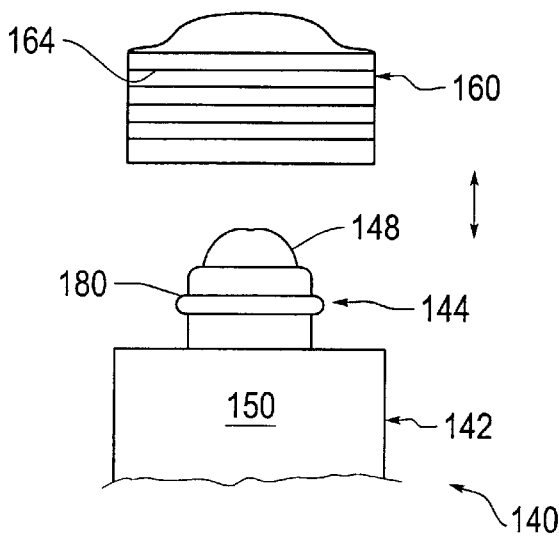
FIG. 4 is a partial elevational view of a 1,1-disubstituted ethylene formulation container that forms another exemplary embodiment of a 1,1-disubstituted ethylene formulation applicator in accordance with the present invention when connected to the applicator tip of FIG. 3.

Another exemplary embodiment of the polymerizable 1,1-disubstituted ethylene monomer formulation container 140 is shown in FIG. 4. The container 140 shown in FIG. 4 differs form the container shown in FIG. 2 in that the male fitting portion 144 of the container body 142 is provided with one or more external elements 180. As illustrated, a single external element 180 is provided in the form of an annular protrusion. As noted above, it should be understood that other configurations of the external element(s) 180 are contemplated that cooperate with the internal element(s) 170 of the applicator tip 100.

The female fitting portion 116 and internal elements 170 of the applicator tip 100 are designed to mate with the male fitting portion 144 and external element 180 of the container 140 to form an applicator according to this invention. In this embodiment, a "snap-fit" arrangement is provided by the internal and external elements 170, 180. It should be noted that the internal and external elements 170, 180 may cooperate to form a tight seal against escape of the formulation 150 from between the male and female fitting portions 144, 116, especially when the internal and external elements 170, 180 are annular.

Although not shown in the foregoing embodiments, it should be understood that the male and female fitting portions 144, 116 may be formed without the screw threads 146, 118 or the external and internal elements 180, 170. For example, the male and female fitting portions 144, 116 may be formed to have a friction-fit.

The female cap member 160 shown in FIG. 4 may be used to close the container 140 prior to use, between uses, and/or after use. The female cap member 160 differs from the cap member shown in FIG. 2 in that the internal threads are appropriately replaced by one or more internal elements (not shown) that mate with the external elements 180. Further, the female cap member 160 includes horizontal ribs or grooves 164 that facilitate removal of the cap member 160 from the container 140.

The exemplary embodiments of the applicator tip 100 and the container 140 shown in FIGS. 3 and 4, respectively, are connected to form a polymerizable 1,1-disubstituted ethylene monomer formulation applicator according to the present invention by separating the female cap member 160 from the male fitting portion 144 of the container 140. If necessary, the dispensing tip 146 is then pierced. (Again, this may be accomplished as described below with respect to the embodiments shown in FIGS. 5 and 6.) Then, the male fitting portion 144 is aligned with the female fitting portion 116 of the applicator tip 100 so that the external element 180 engages the internal elements 170. In the embodiment shown, the external element 180 is releaseably secured between the internal elements 170.

An exemplary embodiment of a polymerizable 1,1-disubstituted ethylene monomer formulation applicator tip 200 is shown in cross section in FIG. 5. The polymerizable 1,1-disubstituted ethylene monomer formulation applicator tip 200 comprises an applicator tip body 210 having an internal cavity 212. The applicator tip body 210 is provided with a substantially planar base 214 at an end of the internal cavity 212. While the exemplary embodiment shown in FIG. 5 includes the base 214, it should be understood that the base 214 is optional.

In embodiments, a porous material member 220 is connected to the applicator tip body 210 so that the porous material member 220 may be in fluid communication with the internal cavity 212. As shown in FIG. 5, when the base 214 is included, the porous material member 220 may be connected to the base 214 and may be sized accordingly. Further, the porous material member 220 may be a sponge as illustrated in FIG. 5, or may be any other suitable material such as a fabric or a membrane.

Further, one or more additives, such as polymerization affecting agents, bioactive agents, colorants or the like, may be included in the porous material member 220. In particular, the entire porous material member 220, or a surface or layer thereof, may be impregnated with the additive(s). For example, an application surface 222 of the porous material member 220 remote from the internal cavity 212 may be coated with the additive(s). In either case, the desired amount of the additive may be determined based on the amount of the polymerizable 1,1-disubstituted ethylene monomer formulation, the particular formulation thereof, or the particular application.

In the exemplary embodiment shown, the porous material member 220 is adjacent to the internal cavity 212, but partially separated from the internal cavity 212 by a breaking or piercing member 290. The piercing member 290 is shown in FIG. 5 as a generally conical portion of the applicator tip body 210. However, it should be understood that any other known or hereafter developed piercing device may be used. For example, a blunt protrusion, a needle (solid or hollow) or a hollow tube may be used. In the exemplary embodiment, the piercing member 290 includes at least one passageway 292 through which the formulation may flow.

A female fitting portion 216 of the applicator tip body 210 defines an end that opens into the internal cavity 212. As shown, the female fitting portion 216 may be opposite the porous material member 220 and substantially surround the piercing member 290. The piercing member 290 may, however, extend partly beyond the female fitting portion 216. The female fitting portion 216 shown in the embodiment of FIG. 5 includes female screw threads 218. In other words, screw threads 218 are formed on an inner surface of the female fitting portion 216. As described above with respect to the embodiment of FIG. 1, the female fitting portion 216 and screw threads 218 are designed to mate with a container, similar to that shown in FIG. 2, to form an applicator according to this invention.

During assembly, or at least once assembled, the piercing member 290 pierces the dispensing tip 148 or other barrier that may be included in the container 140 to prevent the monomer formulation 150 from flowing into the internal cavity 212 before application of the monomer formulation 150 is desired and before the assembly of the applicator is substantially complete. The barrier may be any known or hereafter developed device that is impervious to the formulation and piercable or breakable.

Another exemplary embodiment of a polymerizable 1,1-disubstituted ethylene monomer formulation applicator tip 200 is shown in cross section in FIG. 6. The applicator tip 200 shown in FIG. 6 differs from applicator tip shown in FIG. 5 in that the female fitting portion 216 includes one or more internal elements 270. As illustrated, the internal elements 270 may be two annular protrusions. It should be understood, however, that other configurations of the internal elements 270 are contemplated, such as spaced tabs, annular grooves and/or non-continuous recesses and that only one internal element may be used. As described above with respect to the embodiment of FIG. 3, the female fitting portion 216 and internal elements 270 are designed to mate with a container, similar to that shown in FIG. 4, to form an applicator according to this invention.

The porous material member 120, 220 of the invention preferably comprise a foam pad that dispenses the formulation 150 when compressed, squeezed or otherwise contacted with a surface. The particular material of the foam pad is determined according to the particular application and/or the particular formulation 150. For example, polyurethane foam may be used. In particular, reticulated polyurethane foam and other open cell foams facilitate flow of the monomer formulation 150 through the porous material member 120, 220 to the application surface 122, 222.

Further, the application surface 122, 222 of the invention may be made of a flocculent material, for example a polyester flocculent material, as shown in FIGS. 1, 3, 5 and 6. This makes the application surface 122, 222 soft which is desirable for applications such as the treatment of burns, ulcers, and other sensitive skin injuries. Also, such flocculent material will provide a wicking effect to facilitate the flow of the monomer formulation 150 through the porous material member 120, 220 to the application surface 122, 222.

The foam pad may be fluorinated or otherwise treated to improve stability of the monomer therein. Further, an initiator or accelerator for polymerization of the monomer may be included in the foam pad. As noted above, other additives may be applied to or contained in the foam pad. For example, antiseptic or antimicrobial agents and/or anesthetic agents may be interspersed within the 1,1-disubstituted ethylene monomer formulation at the time of application or at the exact point of application.

It should be understood that the applicators of the present invention may be used to apply more that one material simultaneously by locating different materials at different locations in the particular applicator. For example, a first material may be pre-wetted or applied and dried to the application surface of the porous material member. A second material then may be contained in any one of the porous material member or the monomer container as described above.

An exemplary embodiment of a polymerizable 1,1-disubstituted ethylene monomer formulation applicator kit 300 is shown in FIG. 7. The polymerizable 1,1-disubstituted ethylene monomer formulation applicator kit 300 comprises at least one container of monomer formulation 310 and at least one applicator tip 320. In the embodiment shown, a pair of applicator tips 320 and a pair of containers 310 are part of the kit 300. The applicator tips 320 may have different configurations suitable for different applications or may be relatively similar, even identical, as desired. The containers 310 may be of different sizes and/or formulations, as desired.

The kit 300 may be supplied in a pre-sterilized package. For example, as shown in FIG. 7, the container of monomer formulation 310 and the applicator tip(s) 320 may be contained in a box 330. The box 330 may have a plastic bed 332 with appropriately shaped recesses 334 for the container of monomer formulation 310 and the applicator tip(s) 320. The recesses 334 may include additional notches 336 to facilitate removal of the container of monomer formulation 310 and the applicator tip(s) 320 from the bed 332.

The containers of monomer formulation of the invention are preferably sterile filled. Also, the applicator tips are preferably sterilized, for example, EtO sterilized.

In embodiments, the monomer formulation, the container(s), the applicator tips, the applicator and/or the packaging are preferably sterilized. Sterilization of the monomer formulation, etc. may be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference. Another sterilization method that may be used with the present invention is described in U.S. patent application Ser. No. 09/374,207, filed on Aug. 12, 1999, the entire disclosure of which is incorporated herein by reference. The formulation must show low levels of toxicity to living tissue during its useful life. In particular, the formulation composition may be sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$. Alternatively, or in addition, preservatives may be added to the formulation as described in U.S. patent application Ser. No. 09/430,180 filed on Oct. 29, 1999, the entire disclosure of which is incorporated herein by reference.

Figure 8:
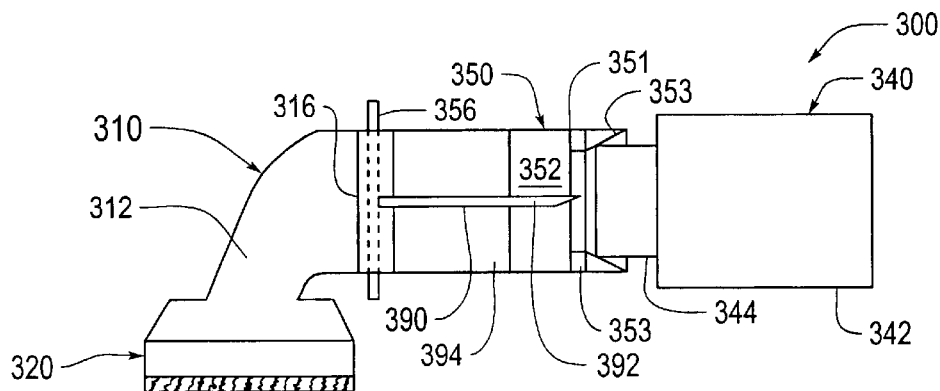
FIG. 8 is a cross-sectional view of another exemplary embodiment of a 1,1-disubstituted ethylene formulation applicator in accordance with the present invention.
Figure 9:
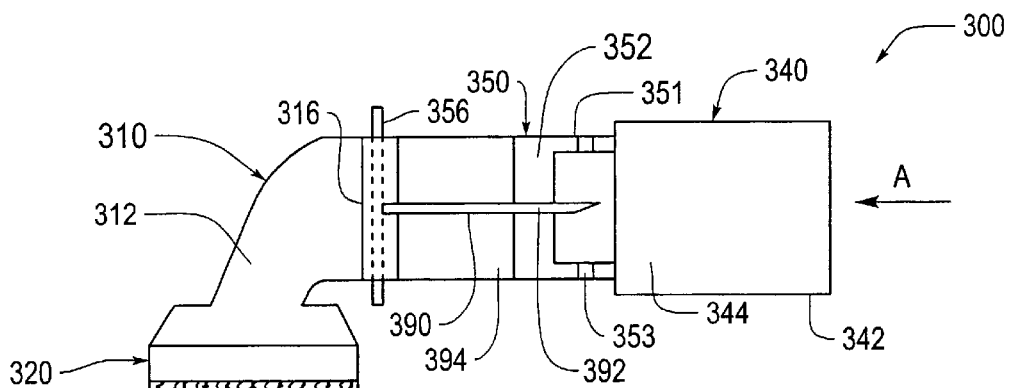
FIG. 9 is a cross-sectional view of the embodiment of FIG. 8 in an activated condition.

An exemplary embodiment of a polymerizable 1,1-disubstituted ethylene monomer formulation applicator 300 is shown in cross section in FIGS. 8 and 9. The polymerizable 1,1-disubstituted ethylene monomer formulation applicator 300 comprises an applicator tip 310 having an internal cavity 312. A porous material member 320 may be connected to the applicator tip 310 to be in fluid communication with the internal cavity 312. The porous material member 320 may include an application surface 322 particularly suited to a desired application need.

It should be understood that the applicator tip 310 may be of any configuration for a desired application. For example, the applicator tip 310 may be angled similar to the applicator tips 100 of FIGS. 1 and 3, may be straight similar to the applicator tips 200 of FIGS. 5 and 6 or may be curved as shown in FIG. 8. Further, it should be understood that the various features, such as a valve member, may or may not be included. Similarly, the arrangement and/or location of various features, such as the porous material member 320, may be varied.

According to the exemplary embodiment of FIGS. 8 and 9, an open end 316 of the applicator tip 310 is connected to a coupler 350. The coupler 350 may comprise a tubular member 351 that provides a conduit 352 in fluid communication with the open end 316 of the applicator tip 310. A piercing member 390 having a passageway 392 is arranged in the coupler 350. For example, the piercing member 390 may be mounted in a support member 394 within the tubular member 351.

One or more retaining members 353 are arranged in the coupler 350 within the tubular member 351. As further described below with respect to FIGS. 10 and 11, the retaining members 353 may be of any suitable configuration, such as an O-ring or a plurality of flaps. Regardless of the particular configuration, at least one of the retaining members 353 is arranged to hold a container of polymerizable 1,1-disubstituted ethylene monomer formulation 340 against or near the piercing member 390. The retaining members 353 preferably serve to align a cap portion 344 of the container of monomer 340 with the piercing member 390.

The cap portion 344 of the container 340 is thus situated in the tubular member 351 of the coupler 350 while a body 342 of the container 340 preferably remains outside. This arrangement allows the shape and size of the body 342 of the container 340 to be determined independently of the configuration of the coupler 350 and/or the applicator tip 310. Thus, any desired amount of the monomer formulation may be provided. Further, since the container 340 is preferably squeezable to dispense the monomer, features of the container 340 that facilitate gripping and/or squeezing of the container 340 may be easily incorporated.

As illustrated, the coupler 350 may include a finger grip 356 that facilitates movement of the container 340 relative to the piercing member 390 from an inactivated position, shown in FIG. 8, to an activated position, shown in FIG. 9. In FIG. 9, the activated position of the container 340 is achieved by moving the container 340 in the direction of the arrow A. Thus, the piercing member 390 punctures the cap portion 344 of the container 340 to release the monomer. The monomer then may flow through the passageway 392, and possibly through the conduit 352, into the internal cavity 312 of the applicator tip 310.

The cap portion 344 may be of any suitably pierceable or breakable configuration. For example, the cap portion 344 may comprise a septum. Alternatively, the cap portion 344 may be scored to be readily pierced or broken. For example, the cap portion 344 may be scored to form inwardly bending flanges when pierced or broken.

Figure 10:
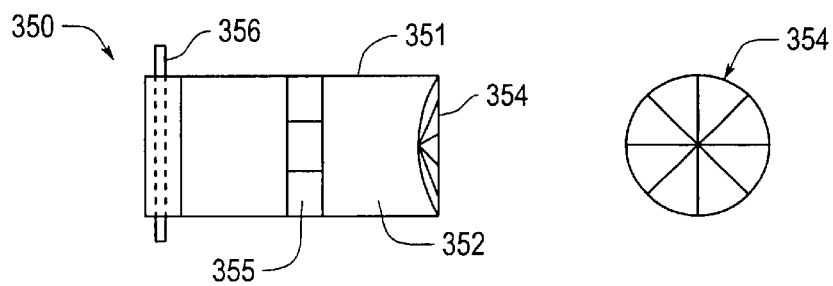
FIG. 10 is a cross-sectional view of the coupler shown in FIG. 8.

The coupler 350 shown in FIGS. 8 and 9 is shown separately in FIG. 10. According to this embodiment, a pair of the retaining members 353 are provided. The first one is shown as a plurality of flaps 354. The plurality of flaps 354 are resiliently bendable inwardly to receive and hold the cap portion 344 of the container 340. The second one is shown as an O-ring 355. The O-ring 355 receives and guides the cap portion 344 while the container 340 is moved in the direction of arrow A. Once the container 340 is in the activated position, the O-ring 355 resists movement to the inactivated position.

Figure 11:
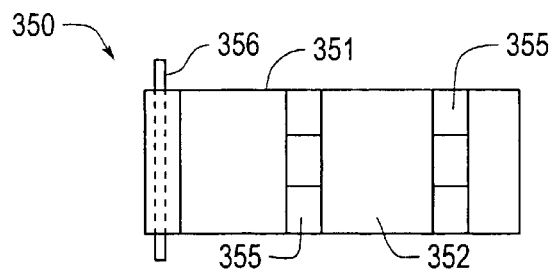
FIG. 11 is another exemplary embodiment of a coupler according to the present invention.
Figure 12:
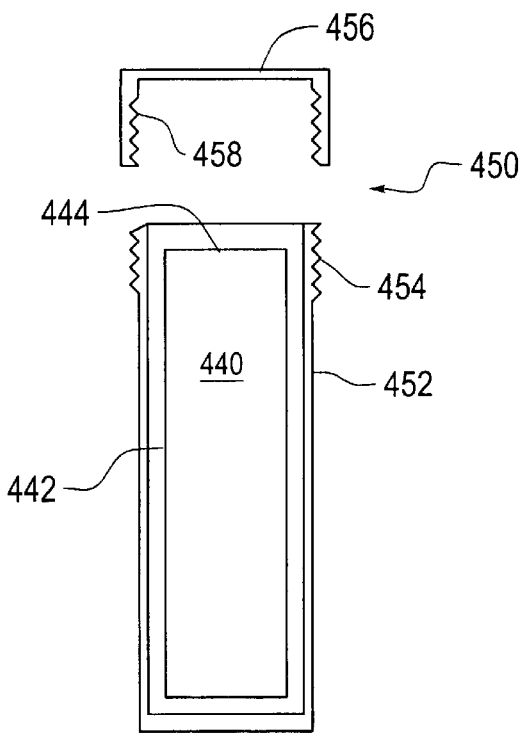
FIG. 12 is a cross-sectional view of an exemplary embodiment of a casing and cartridge in accordance with the present invention.

While both the O-ring 355 and the plurality of flaps 354 are shown in the embodiments of FIGS. 8–10, only one or the other may be used as desired. For example, an alternative embodiment of the coupler 350 is shown in FIG. 11. In this embodiment, both of the retaining members are O-rings 355.

A single retaining member may be used as well. For example, the single retaining member may be arranged to move within the tubular member 351 of the coupler 350. In such a case, the single retaining member moves with the cap portion 344 of the container 340 to guide the cap portion 344 to the piercing member 390.

An exemplary embodiment of a polymerizable 1,1-disubstituted ethylene monomer formulation applicator is shown in FIGS. 12–16. According to this embodiment, a casing 450 is provided for receiving a container or cartridge of polymerizable 1,1-disubstituted ethylene monomer formulation 440. The casing 450 comprises a casing body 452 having a male fitting 454 at an open end. The casing 450 may further comprise a casing cap 456 having a female fitting 458 corresponding to the male fitting 454. Although shown as screw threads, the male and female fittings 454, 458 may have any suitable configuration. For, example a press-fit or a friction-fit may be used as well.

The casing 450 may be used to protect the cartridge 440 prior to use. During use, as described below, the casing 450 serves as a handle for the applicator and protects against spillage of the monomer.

Figure 13:
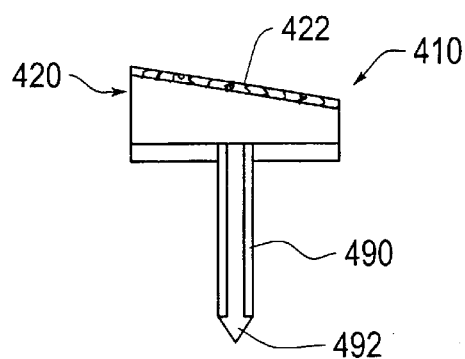
FIG. 13 is a cross-sectional view of an exemplary embodiment of an applicator tip in accordance with the present invention.
Figure 14:
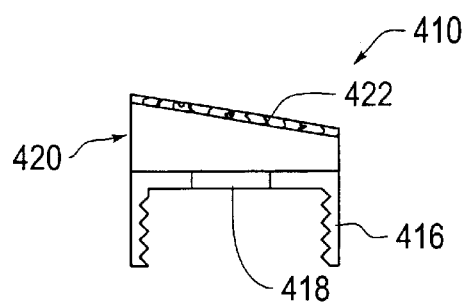
FIG. 14 is another exemplary embodiment of an applicator tip in accordance with the present invention.
Figure 15:
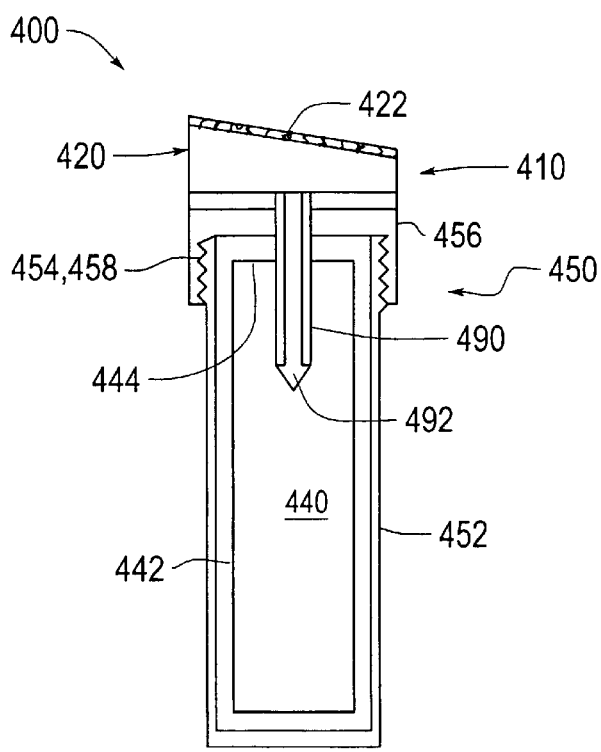
FIG. 15 is a cross-sectional view of an exemplary embodiment of an applicator formed by combining the casing and cartridge of FIG. 12 with the applicator tip of FIG. 13.
Figure 16:
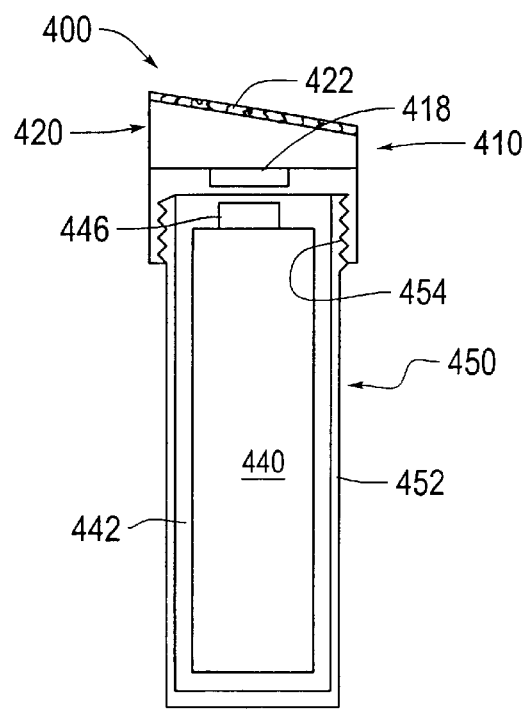
FIG. 16 is a cross-sectional view of an exemplary embodiment of an applicator formed by combining the casing and cartridge of FIG. 12 with the applicator tip of FIG. 14.

An applicator tip 410, as shown in FIGS. 13 and 14, may be used in conjunction with the casing 450 to form an applicator 400, as shown in FIGS. 15 and 16, respectively. The exemplary applicator tip 410 shown in FIG. 13 includes a piercing member 490 with a passageway 492. The applicator tip 410 may also include a porous material member 420 with an application surface 422, as shown. It should be understood, however, that other features or arrangements of features may be included. For example, the applicator tip 410 may include a valve member and/or a female fitting as described in previous embodiments.

As shown in FIG. 15, the applicator tip 410 may be attached to the casing cap 456 so that the piercing member 490 pierces the cap 456 and pierces or breaks a pierceable or breakable end 444 of the cartridge of monomer 440, allowing the monomer to flow through the passageway 492 into the porous material member 420. The end of the cartridge 440 that is to be pierced, and the casing cap 456 too, may include a central portion that is relatively thin or weak to facilitate piercing. For example, the end may be scored or may be formed by a septum.

The exemplary applicator tip 410 shown in FIG. 14 includes an opening 418 rather than a piercing member with a passageway. Again, the applicator tip 410 may also include a porous material member 420 with an application surface 422, as shown. The exemplary applicator tip 410 shown in FIG. 14 also includes a female fitting 416, similar to the casing cap 456, for mating with the male fitting 454 of the casing body 452.

As shown in FIG. 16, the applicator tip 410 may be attached directly to the casing cap 456. The cartridge of monomer 440 in this exemplary embodiment includes an open end 446. The open end 446 may be kept closed by a cap (not shown) prior to intended use. Such a cap may be incorporated into the casing cap 456 is desired. According to this embodiment, the casing cap 456 is replaced by the applicator tip 410 to form the applicator 400. The open end 446 allows the monomer to flow through the opening 418 into the porous material member 420.

In both of the embodiments shown in FIGS. 15 and 16, the casing 450 and cartridge 440 may be squeezable to control dispensing of the monomer. Also, even after the applicator tip 410 is attached to form the applicator 400, the casing cap 456 may be removed along with the applicator tip 410 to replace the cartridge 440. Thus, the amount of monomer that may be applied by the applicator 400 is not limited to by volume of the casing 450.

Figure 17:
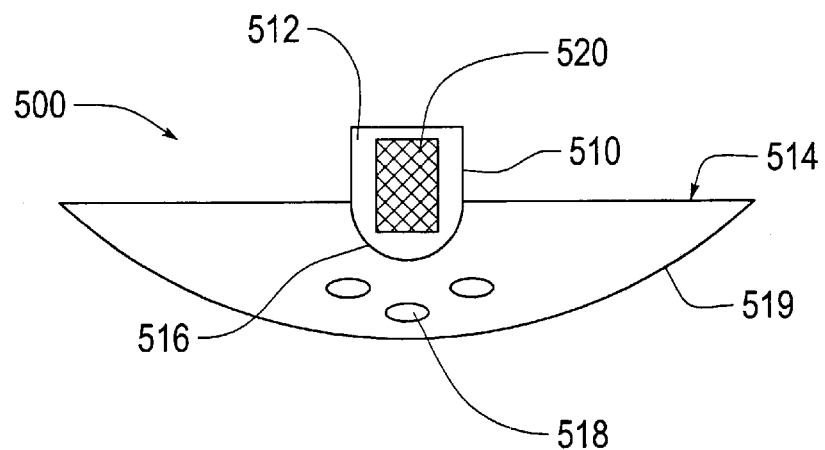
FIG. 17 is a cross-sectional view of another exemplary embodiment of an applicator tip in accordance with the present invention.
Figure 18:
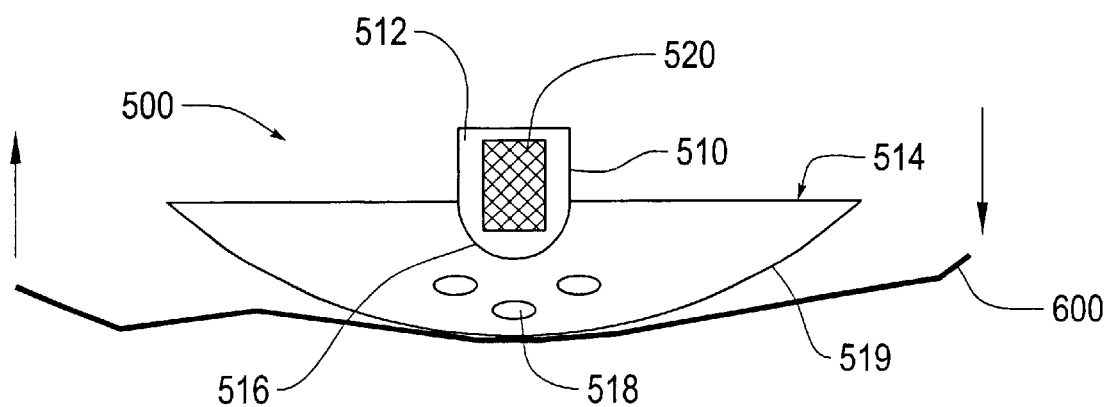
FIG. 18 illustrates the embodiment of FIG. 17 when in use.

FIGS. 17 and 18 show an exemplary embodiment of an applicator tip/attachment 500 in cross section. While this embodiment is referred to as an attachment because it may cooperate with an existing applicator tip, it should be understood that the applicator attachment 500 may be an applicator tip that is attached to a container in any suitable manner, such as with screw threads. In any case, the applicator tip/attachment 500 is preferably reusable. Thus, the applicator tip/attachment 500 should be cleanable, for example with a solvent, and sterilizable, for example chemically.

The applicator attachment 500 comprises a body 510 with a cavity 512. A head portion 514 is movably attached to the body 510 by a swivel or hinge connection 516. One or more openings 518 allow the monomer to reach an application surface 519 of the head portion 514. Alternatively, the head portion 514 may be made of a porous material.

As illustrated in FIG. 18, the connection 516 allows the head portion 514 to move to follow the contours of the application site 600, such as wounded tissue. This facilitates application of the monomer. Further, the head portion 514 may be smooth and rounded to reduce disadvantageous friction and allow the applicator to glide over the surface of the application site 600. The head portion 514 may be any size or shape as desired. In embodiments, for example, the head portion 514 may be trowel-shaped or disc-shaped. Further, the head portion 514 may be rounded at one end and more pointed at another. The head portion 514 may be made of high density plastic, aluminum, fluoropolymer (e.g., Teflon™), porous material (e.g., Porex™) or any other material that is compatible with the monomer formulation(s) used, a corresponding solvent(s) or both.

It should be understood that the individual features described with respect to the various exemplary embodiments of the applicators and the applicator tips may be included or excluded as desired. As such, all possible combinations of the described features are considered to be encompassed by the present invention.

Thus, while the present invention has been described in terms of exemplary embodiments, it is to be understood that the present invention is not to be limited to the particular configuration of these embodiments. One skilled in the art will recognize that various modifications and/or alterations of these embodiments may be made while remaining within the scope of the present invention.

What is claimed is:

1. A polymerizable 1,1-disubstituted ethylene monomer formulation applicator, comprising:
    an applicator tip with an internal cavity capable of receiving a polymerizable 1,1-disubstituted ethylene monomer, the applicator tip having a female fitting that defines an open end communicating with the internal cavity, the applicator tip including a porous application surface; and
    a container of polymerizable 1,1-disubstituted ethylene monomer, the container having a male fitting that is engaged with the female fitting so that the container is in fluid communication with the internal cavity during use.

2. The applicator of claim 1, wherein the male fitting is engaged with the female fitting by a friction-fit.

3. The applicator of claim 1, wherein the female fitting includes female screw threads and the male fitting includes male screw threads.

4. The applicator of claim 1, wherein the female fitting includes at least one internal element and the male fitting include at least one external element, the internal and external elements being complementary so as to engage the male fitting with the female fitting.

5. The applicator of claim 4, wherein the internal and external elements are annular.

6. The applicator of claim 4, wherein the internal and external elements comprise a snap-fit arrangement.

7. The applicator of claim 4, wherein the internal and external elements provide a friction-fit.

8. The applicator of claim 1, wherein an inner surface of the container includes a polymerization or cross-linking inhibitor for the monomer in or on an inner surface of the container.

9. The applicator of claim 1, wherein the container comprises a material providing storage stability for the monomer.

10. The applicator of claim 1, further comprising:
    a 1,1-disubstituted ethylene impermeable barrier adjacent the male fitting of the container.

11. The applicator of claim 10, further comprising:
    a piercing or breaking member disposed substantially within the internal cavity, the piercing or breaking member arranged to pierce or break the barrier when the male fitting is engaged with the female fitting.

12. The applicator of claim 11, wherein the piercing member includes at least one passageway.

13. The applicator of claim 1, further comprising:
    a polymerization affecting agent for the monomer in or on the porous application surface.

14. The applicator of claim 1, wherein the porous application surface comprises a flocculent material.

15. The applicator of claim 14, wherein the flocculent material comprises polyester.

16. The applicator of claim 1, wherein the porous application surface comprises a porous material member in fluid communication with the internal cavity.

17. The applicator of claim 16, further comprising:
   a polymerization affecting agent for the monomer in the porous material member.

18. The applicator of claim 1, wherein the applicator tip further comprises a porous material member in fluid communication with the internal cavity.

19. The applicator of claim 18, wherein the porous material member is disposed within the internal cavity.

20. The applicator of claim 19, further comprising:
   a polymerization affecting agent for the monomer in the porous material member.

21. The applicator of claim 18, wherein an application surface of the porous material member comprises a flocculent material.

22. The applicator of claim 21, wherein the flocculent material is polyester.

23. The applicator of claim 18, wherein the porous material member is selected from the group consisting of a sponge, a foam pad, a fabric and a membrane.

24. The applicator of claim 18, wherein the porous material member comprises an open cell foam pad.

25. The applicator of claim 24, wherein an application surface of the open cell foam pad comprises a flocculent material.

26. The applicator of claim 25, wherein the flocculent material is polyester.

27. The applicator of claim 18, wherein the porous material member comprises a reticulated polyurethane foam pad.

28. The applicator of claim 27, wherein an application surface of the reticulated polyurethane foam pad comprises a flocculent material.

29. The applicator of claim 28, wherein the flocculent material is polyester.

30. The applicator of claim 1, wherein the applicator tip further comprises:
   a valve member disposed between the internal cavity and an application surface of the applicator tip to selectively place the application surface in fluid communication with the internal cavity.

31. The applicator of claim 30, wherein the valve member comprises a pressure-controlled valve.

32. The applicator of claim 30, wherein the valve member comprises a flexible slit.

33. The applicator of claim 30, wherein the container is squeezable to actuate the valve member.

34. A method of applying a polymerizable 1,1-disubstituted ethylene monomer formulation to tissue, comprising:
   connecting the application tip and the container of polymerizable 1,1-disubstituted ethylene monomer formulation of claim 1;
   releasing the polymerizable 1,1-disubstituted ethylene monomer from the container into the internal cavity of the applicator tip; and
   applying the monomer from the porous material member directly to the tissue.

35. The method of claim 34, wherein the tissue has been subjected to a laser ablation procedure.

36. The method of claim 34, wherein the tissue has been burned.

37. The method of claim 34, wherein the tissue is ulcerous.

38. The method of claim 34, wherein the tissue comprises decubitus ulcers.

39. A polymerizable 1,1-disubstituted ethylene monomer formulation applicator, comprising:
   an applicator tip with an internal cavity capable of receiving a polymerizable 1,1-disubstituted ethylene monomer;
   a container of polymerizable 1,1-disubstituted ethylene monomer, the container being movably connected to the applicator tip; and
   a 1,1-disubstituted ethylene monomer impermeable barrier preventing fluid communication between the container and the internal cavity of the applicator tip prior to use.

40. The applicator of claim 39, further comprising:
   a piercing or breaking member disposed substantially within the internal cavity.

41. The applicator of claim 40, wherein the piercing member includes at least one passageway.

42. The applicator of claim 39, wherein an inner surface of the container includes a polymerization or cross-linking inhibitor for the monomer in or on an inner surface of the container.

43. The applicator of claim 39, wherein the container comprises a material providing storage stability for the monomer.

44. The applicator of claim 39, wherein the applicator tip comprises a porous application surface.

45. The applicator of claim 44, further comprising:
   a polymerization affecting agent for the monomer in or on the porous application surface.

46. The applicator of claim 44, wherein the porous application surface comprises a flocculent material.

47. The applicator of claim 46, wherein the flocculent material comprises polyester.

48. The applicator of claim 44, wherein the porous application surface comprises a porous material member in fluid communication with the internal cavity.

49. The applicator of claim 48, further comprising:
   a polymerization affecting agent for the monomer in the porous material member.

50. The applicator of claim 44, wherein the applicator tip further comprises a porous material member in fluid communication with the internal cavity.

51. The applicator of claim 50, wherein the porous material member is disposed within the internal cavity.

52. The applicator of claim 51, further comprising:
   a polymerization affecting agent for the monomer in the porous material member.

53. The applicator of claim 50, wherein an application surface of the porous material member comprises a flocculent material.

54. The applicator of claim 53, wherein the flocculent material is polyester.

55. The applicator of claim 50, wherein the porous material member is selected from the group consisting of a sponge, a foam pad, a fabric and a membrane.

56. The applicator of claim 50, wherein the porous material member comprises an open cell foam pad.

57. The applicator of claim 56, wherein an application surface of the open cell foam pad comprises a flocculent material.

58. The applicator of claim 57, wherein the flocculent material is polyester.

59. The applicator of claim 50, wherein the porous material member comprises a reticulated polyurethane foam pad.

60. The applicator of claim 59, wherein an application surface of the reticulated polyurethane foam pad comprises a flocculent material.

61. The applicator of claim 60, wherein the flocculent material is polyester.

62. The applicator of claim 39, wherein the applicator tip further comprises:

a valve member disposed between the internal cavity and an application surface of the applicator tip to selectively place the application surface in fluid communication with the internal cavity.

63. The applicator of claim 62, wherein the valve member comprises a pressure-controlled valve.

64. The applicator of claim 62, wherein the valve member comprises a flexible slit.

65. The applicator of claim 62, wherein the container is squeezable to actuate the valve member.

66. A method of applying a polymerizable 1,1-disubstituted ethylene monomer formulation to tissue, comprising:

connecting the application tip and the container of polymerizable 1,1-disubstituted ethylene monomer formulation of claim 39;

releasing the polymerizable 1,1-disubstituted ethylene monomer from the container into the internal cavity of the applicator tip; and applying the monomer from the applicator tip directly to the tissue.

67. The method of claim 66, wherein the tissue has been subjected to a laser ablation procedure.

68. The method of claim 66, wherein the tissue has been burned.

69. The method of claim 66, wherein the tissue is ulcerous.

70. The method of claim 66, wherein the tissue comprises decubitus ulcers.

* * * * *

UNITED STATES PATENT AND TRADEMARK OFFICE
Certificate

Patent No. 6,439,789 B1                                                       Patented: August 27, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Jerry Balance, Willow Spring, NC; Daniel L. Hedgpeth, Raleigh, NC; Jeffrey G. Clark, Raleigh, NC; William Cotter, Raleigh, NC; and Keith R. D'Alessio, Cary, NC.

Signed and Sealed this Twenty-third Day of September 2003.

*GREGORY L. HUSON*
*Acting Supervisory Patent Examiner*
*Art Unit 3751*